(12) United States Patent
Hasse et al.

(10) Patent No.: US 9,468,615 B2
(45) Date of Patent: Oct. 18, 2016

(54) USE OF MALONONITRILAMIDES IN NEUROPATHIC PAIN

(71) Applicant: AL-GIAX Pharmaceuticals GMBH, Erkrath (DE)

(72) Inventors: Birgit Hasse, Wuppertal (DE); Guido Koopmans, Sittard (NL)

(73) Assignee: Algiax Pharmaceuticals GmbH, Erkrath (DE)

( * ) Notice: Subject to any disclaimer, the term of this patent is extended or adjusted under 35 U.S.C. 154(b) by 0 days.

(21) Appl. No.: 14/328,035

(22) Filed: Jul. 10, 2014

(65) Prior Publication Data

US 2014/0357722 A1    Dec. 4, 2014

Related U.S. Application Data

(62) Division of application No. 13/880,139, filed as application No. PCT/EP2011/005452 on Oct. 28, 2011, now abandoned.

(60) Provisional application No. 61/408,195, filed on Oct. 29, 2010.

(30) Foreign Application Priority Data

Oct. 29, 2010 (EP) .................................... 10014122

(51) Int. Cl.
| | |
|---|---|
| *A01N 37/00* | (2006.01) |
| *A61K 31/165* | (2006.01) |
| *A61K 31/167* | (2006.01) |
| *A61K 31/275* | (2006.01) |
| *A61K 31/164* | (2006.01) |
| *A61K 31/42* | (2006.01) |

(52) U.S. Cl.
CPC ........... *A61K 31/167* (2013.01); *A61K 31/164* (2013.01); *A61K 31/275* (2013.01); *A61K 31/42* (2013.01)

(58) Field of Classification Search
CPC ............. A61K 31/164; A61K 31/167; A61K 31/275; A61K 31/42
See application file for complete search history.

(56) References Cited

U.S. PATENT DOCUMENTS

| | | |
|---|---|---|
| 5,308,865 A | 5/1994 | Bartlett |
| 5,532,259 A | 7/1996 | Bartlett |
| 2003/0223960 A1 | 12/2003 | Wettstein |

FOREIGN PATENT DOCUMENTS

| | | |
|---|---|---|
| FR | 2727628 | 6/1996 |
| WO | 9117748 | 11/1991 |
| WO | 0071113 | 11/2000 |
| WO | 2012025217 | 3/2012 |

OTHER PUBLICATIONS

McPherson, Medscape, Neuropathic Pain: An Update on Effective Management, May 3, 2007.*
Afridi and Goadsby, "New onset migraine with a brain stem cavernous angioma", J. Neurosurg. Psychiatry, 74:680-2 (2003).
Attal, et al., "The bidirectional dose-dependent effect of systemic naloxone is also related to the intensity and duration of pain-related disorders: a study in a rat model of peripheral mononeuropath", Brain Res., 525:170-40 (1990).
Attal, et al., "Chronic neuropathic pain management in spinal cord injury patients. What is the efficacy of pharmacological treatments with a generalmode of administration? (oral, transdermal, intravenous)", Ann, Phys. Rehabul. Med., 52(2):124-41 (2009).
Bennet and Xie, "A peripheral mononeuropathy in rat that produces disorders of pain sensation like those seen in man", Pain, 33:87-107 (1988).
Cao and DeLeo, "CNS-infiltrating CD4+ T lymphocytes contribute to murine spinal nerve transection-induced neuropathic pain", Eur. J. Immunol., 38:448-58 (2008).
Chaplan, et al., "Quantitative assessment of tactile allodynla in the rat paw", J Neurosci Methods, 53:56-63 (1994).
Collins, et al., "NMDA receptor antagonists for the treatment of neuropathic pain", Pain Med., 11(11):1726-42 (2010).
Costigan, et al., "T-cell infiltration and signaling in the adult dorsal spinal cord is a major contributor to neuropathic pain-like hypersensitivity", J Neurosci., 29:14415-22 (2009).
Davis, et al., "The immunosuppressive metabolite of leflunomide is a potent inhibitor of human dihydroorotate dehydrogenase", Biochem., 35:1270-3 (1996).
De La Calle, et al., "Intrathecal transplantation of neuroblastoma cells decreases heat hyperalgesia and cold allodynia in a rat model of neuropathic pain", Brain Res. Bull., 59:205-11 (2002).
Goadsy, "Neurovascular headache and a midbrain vascular malformation: evidence for a role of the brainstem in chronic migraine", Cephalalgia, 22:107-11 (2002).
Gruner, "A monitored contusion model of spinal cord injury in the rat", J. Neurotrama., 9(2):126-8 (1992).
Greene, et al., "Inhibition of dihydroorotate dehydrogenase by the Immunosuppressive agent leflunomide", Biochem. Pharmacol., 60:861-7 (1995).
Kao, et al., "Synthesis, structure-activity relationships, and pharmacokinetic properties of dihydroorotate dehydrogenase inhibitors: 2-cyano-3-cyclopropyl-3-hydroxy-N-[3'-methyl-4'-(trifluoromethyl)phenyl ) propenamide and related compounds", J. Med. Chem., 39:4608-21 (1996).
Schorlemmer, et al., "Therapeutic activity of malononitrilamides (MNA 279 and MNA 715) on acute and chronic, relapsing, experimental, allergic encephalomyelitis (EAE)", Drug Exp Clin. Res., 23(5-6)175-81 (1997).

(Continued)

*Primary Examiner* — Jean Cornet
(74) *Attorney, Agent, or Firm* — Ballard Spahr LLP

(57) ABSTRACT

Provided herein are compounds and pharmaceutical compositions for use in the treatment of neuropathic pain and the neuropathic pain syndromes.

5 Claims, 9 Drawing Sheets

(56) References Cited

OTHER PUBLICATIONS

Seltzer, et al., "A novel behavioral model of neuropathic pain disorders produced in rats by partial sciatic nerve injury", Pain, 43:205-18 (1990).

Williamson, et al., "Dihydroorotate dehydrogenase is a high affinity binding protein for A77 1726 and mediator of a range of biological effects of the immunomodulatory compound", J. Biol. Chem., 270:22467-72 (1995).

Zenonos and Kim, "A T cell-orchestrated immune response in the adult dorsal spinal cord as a cause of neuropathic pain-like hypersensitivity after peripheral nerve damage: a door to novel therapies", Neurosurgery, 66(4):N24-5 (2010).

Zielinski, et al., "Leflunomide, a reversible inhibitor of pyrimidine biosynthesis", Inflamm. Res., 44(Supp2):S207-8 (1995).

Curnock, et al., "Potencies of leflunomide and HR325 as inhibitors of prostaglandin endoperoxide H synthase-1 and -2: comparison with nonsteroidal anti-inflammatory drugs", J Pharmacol Exp Ther., 282(1):339-47 (1997).

Glomsda, et al., "Inhibition of monocyte/endothelial cell interactions and monocyte adhesion molecule expression by the immunosuppressant mycophenolate mofetil", Spinal Cord, 41:610-9 (2003).

Neva, Cervical spine changes in rheumatoid arthritis, Academic Disseration, Acta University of Tampere, 1-86 (2001).

Schrepfer, et al., "FK778, a novel immunosuppressive agent, reduces early adhesion molecule up-regulation and prolongs cardiac allograft survival", Transpl. Int., 18(2):215-20 (2005).

Sweitzer and DeLeo, "The active metabolite of leflunomide, an immunosuppressive agent, reduces mechanical sensitivity in a rat mononeuropathy model", J Pain, 3(5):360-8 (2002).

Tessler and Murray, "Cyclosporine A, FK506", J Japanese Orthopedic Assoc., 80(8):S907,1-P3-2 (2006).

* cited by examiner

USE OF MALONONITRILAMIDES IN NEUROPATHIC PAIN

FIELD OF THE DISCLOSURE

The technology provided herein relates to the novel use of malononitrilamides and its derivatives in the treatment of neuropathic pain and neuropathic pain syndromes.

BACKGROUND

The treatment of pain conditions is of great importance in medicine. There is currently a world-wide need for additional pain therapy. The pressing requirement for a specific treatment of pain conditions is documented in the large number of scientific works that have appeared recently in the field of applied analgesics.

Pain is defined by the International Association for the Study of Pain (IASP) as "an unpleasant sensory and emotional experience associated with actual or potential tissue damage, or described in terms of such damage". Although pain is always subjective, its causes or syndromes can be classified. One of the most relevant pains is neuropathic pain which severely impairs the overall quality of life, and which is one of the most devastating forms of chronic pain.

Neuropathic pain is caused by, for example, injury of dysfunction in a peripheral or central nervous system. Disorders with neuropathic pain include, for example, disorders that exhibit hyperalgesic or allodynic symptoms, such as postherpetic neuralgia, trigeminal neuralgia, diabetic neuralgia, and persistent postoperative or posttraumatic pain.

Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain.

Peripheral nerve injury or dysfunction can result in peripheral neuropathic pain. Examples are mononeuropathies (e.g., carpal tunnel syndrome, radiculopathy), plexopathies (typically caused by nerve compression, as by a neuroma, tumor, or herniated disk), and polyneuropathies (typically caused by various metabolic neuropathies. Under normal circumstances, pain sensations are carried by unmyelinated and thinly myelinated nerve fibers, designated C-fibers and A-delta fibers respectively. After a peripheral nervelesion, a neuroma may develop at the stump. The neurons become unusually sensitive and develop spontaneous pathological activity, abnormal excitability, and elevated sensitivity to chemical, thermal and mechanical stimuli. This phenomenon is called peripheral sensitization.

Central neuropathic pain is found in spinal cord injury, multiple sclerosis, and in some cases of stroke. In the spinal cord the spinothalamic tract (STT) constitutes the major ascending nociceptive pathway. As a consequence of ongoing spontaneous activity arising in the periphery, STT neurons in the dorsal horn develop an increased background activity, enlarged receptive field and increased responses to afferent impulses, including normally innocuous tactile stimuli. This phenomenon is called central sensitization. Central sensitization has beers proposed as an important mechanism of persistent neuropathic pairs. Non-neural glial cells and the immune response play a prominent role in central sensitization.

Typical symptoms of neuropathic pain are dysesthesias (spontaneous or evoked burning pain, often with a superimposed lancinating component), but pain may also be deep and aching. Other sensations like; hyperesthesia, hyperalgesia, allodynia (pain due to a nonnoxious stimulus), and hyperpathia (particularly unpleasant, exaggerated pain response) may also occur. Symptoms are long-lasting, typically persisting after resolution of the primary cause (if one was present) because the CNS has been sensitized and remodeled.

Peripheral nerve injury provokes a reaction in peripheral immune cells and glia at several different anatomical locations: macrophages and Schwann cells facilitate the wallerian degeneration of axotomized nerve fibers distal to a nerve lesion; an immune response in the dorsal root ganglia (DRGs) is driven by macrophages, lymphocytes and satellite cells; activation of spinal microglia dominates the early glial response in the CNS to peripheral nerve injury, which is followed by activation and proliferation of astrocytes. More recently, a specific role of the immune response and CNS-infiltrating T lymphocytes in nerve injury induced neuropathic pain development and maintenance has been identified (Cao and DeLeo, 2008; Costigan et al., 2009; Zenonos and Kim).

Migraine is a common head pain syndrome, often genetically determined, characterized by generally episodic hut often chronic, usually throbbing pain, often unilateral in distribution and often associated with photophobia, phonophobia, osmophobia, nausea and/or vomiting. The common occurrence of throbbing head pain was wrongly interpreted earlier for the pain to arise from blood vessels; but current research points to a neural origin of the migraine pain. Several observations made over the past two decades raised the issue that there is likely to be a central pain mechanism in migraine (Afridi and Goadsby, 2003; Goadsby, 2002).

Current therapy for neuropathic pain aims only at reducing symptoms, generally by suppressing neuronal activity. Thus treatment options, e.g. NSAIDS, antidepressants, anticonvulsants, baclofen, neuromodulation modalities or opiates, predominantly alleviate symptoms via nonspecific reduction of neuronal hyperexcitability rather than targeting the specific etiologies.

Therefore, effective and improved methods and compounds that we able to treat neuropathic pain are needed.

SUMMARY OF THE DISCLOSURE

In a first aspect, embodiments of this disclosure provide compounds for the use in the treatment of neuropathic pain and/or neuropathic pain syndromes.

In still another aspect, embodiments of this disclosure provide pharmaceutical compositions, single unit dosage forms, and kits suitable for use in the treatment of neuropathic pain which comprise compounds according to the present disclosure.

In a further aspect, embodiments of this disclosure relate to methods of treating and preventing neuropathic pain which comprise administering to a patient in need of such treatment or prevention a therapeutically or prophylactically effective amount of a compound according to this disclosure.

Further, embodiments of this disclosure relates to malononitrilamides, or its derivatives, pharmaceutically acceptable salts, solvates, hydrates, stereoisomers, tautomers clathrates, or prodrugs thereof for use in the treatment of neuropathic pain.

DETAILED DESCRIPTION OF THIS DISCLOSURE

Figure 1:
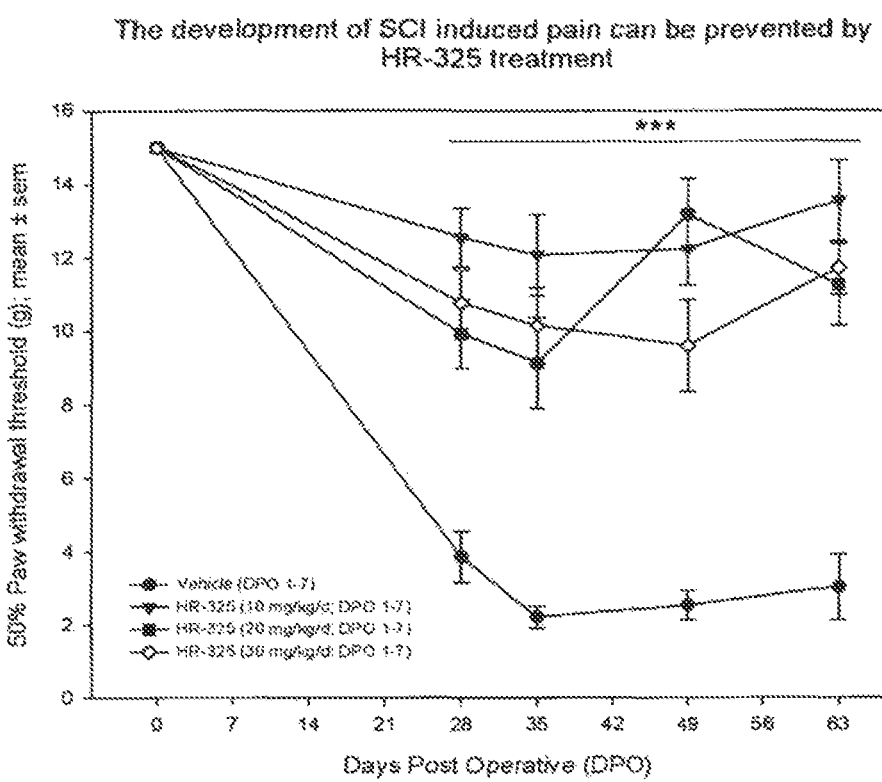
FIG. 1 shows the 50% paw withdrawal threshold (g) after contusion and oral gavage of HR325 and vehicle.

Disclosed herein is the use of malononitrilamides for the treatment of neuropathic pain.

Neuropathic pain according to the present disclosure is a pain initiated or caused by a primary lesion or dysfunction in the nervous system.

For example, neuropathic pain syndromes include postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., postmastectomy syndrome, postthoracotomy syndrome, phantom pain), and complex regional pain syndrome (reflex sympathetic dystrophy and causalgia).

In advantageous embodiments of the present disclosure, the neuropathic pain have typical symptoms like dysesthesias (spontaneous or evoked burning pain, often with a superimposed lancinating component), but pain may also be deep and aching. Other sensations like; hyperesthesia, hyperalgesia, allodynia (pain due to a nonnoxious stimulus), and hyperpathia (particularly unpleasant, exaggerated paid response) may also occur.

Neuropathic pain according to the present disclosure could be divided into "peripheral" (originating in the peripheral nervous system) and "central" (originating in the brain or spinal cord).

In advantageous embodiments, the central neuropathic pain is of a type that has a cause that is selected from the following group of causes:
cerebral lesions that are predominantly thalamic;
infarction, e.g. thalamic infarction or brain stem infarction;
cerebral tumors or abscesses compressing the thalamus or brain stem;
multiple sclerosis;
brain operations, e.g. thalamotomy in cases of motoric disorders;
spinal cord lesions;
spinal cord injuries;
spinal cord operations, e.g. anterolateral cordotomy;
ischemic lesions;
anterior spinal artery syndrome;
Wallenberg's syndrome; and
syringomyelia.

In an advantageous embodiment according to the present disclosure the neuropathic pain is a central neuropathic pain syndrome. In some examples the central neuropathic pain syndrome is caused by spinal cord injury and/or spinal cord contusion (see example 1 to 3).

In a further advantageous embodiment of the present disclosure the neuropathic pain is a head pain syndrome caused by central pain mechanisms like in migraine or migraine pain.

In further advantageous embodiments the neuropathic pain is a peripheral neuropathic pain. In some examples, the peripheral neuropathic pain is caused by chronic constriction injury or by ligation of the sciatic nerve (see example 4 and 5).

According to the present disclosure the predominantly peripheral neuropathic pain includes a type that is selected from the following types of neuropathic pain and/or has a cause that is selected from the group of the following causes:
systemic diseases, e.g. diabetic neuropathy;
drug-induced lesions, e.g. neuropathy due to chemotherapy;
traumatic syndrome and entrapment syndrome;
lesions in nerve roots and posterior ganglia;
neuropathies after HIV infections;
neuralgia after Herpes infections;
nerve roof avulsions;
cranial nerve lesions;
cranial neuralgia, e.g., trigeminal neuralgia;
neuropathic cancer pain;
phantom pain;
compression of peripheral nerves, neuroplexus and nerve roots;
paraneoplastic peripheral neuropathy and ganglionopathy;
complications of cancer therapies, e.g. chemotherapy, irradiation, and surgical interventions;
complex regional pain syndrome;
type I lesions (previously known as sympathetic reflex dystrophy); and
type II lesions (corresponding approximately to causalgia)

In advantageous embodiments, the compounds used for the treatment of neuropathic pain and/or neuropathic pain syndromes are malononitrilamides or pharmaceutically acceptable salts, solvates, tautomers or stereoisomers thereof.

Specific examples of compounds used for the treatment of neuropathic pain syndromes include, but not limited to compounds with the following structures (formula II to IV):

I)

HR325

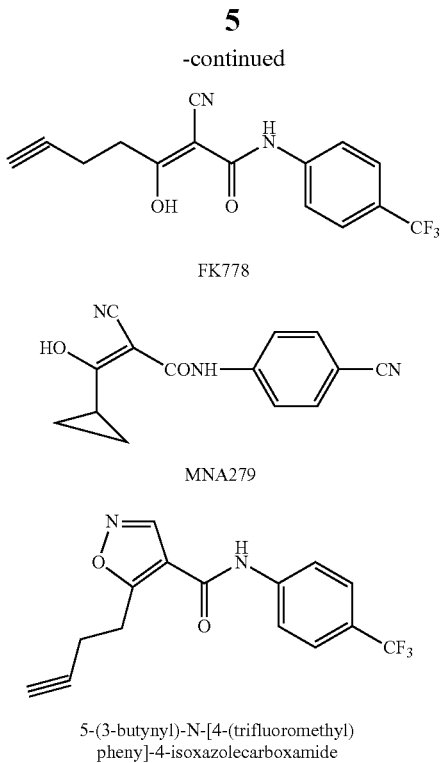

FK778

MNA279

5-(3-butynyl)-N-[4-(trifluoromethyl)
phenyl]-4-isoxazolecarboxamide

In further advantageous embodiments, the compound is selected front the group consisting of 1(3-methyl-4-trifluoro methylphenyl-carbamoyl)-2-cyclopropyl-2oxo-propionitrile, N-(4-trifluoromethyl)-phenyl-2-cyano-3-hydroxy-hept-2-en-6-in-carboxylic acidamide, 5-(3-butyl)-N-[4-(trifluoromethyl) phenyl]-4-isoxazolecarboxamide and 2-cyano-3-cyclopropyl-3-oxo-(4-cyanophenyl)propionamide or a pharmaceutically acceptable salt, solvate, tautomer or stereoisomer thereof.

In advantageous embodiments, the compound is 1(3-methyl-4-trifluoro methylphenyl-carbamoyl)-2-cyclopropyl-2oxo-propionitrile.

In another advantageous embodiment, the compound is N-(4-trifluoromethyl)-phenyl-2-cyano-3-hydroxy-hept-2-en-6-in-carboxylic acidamide.

In further advantageous embodiments, the compound has the structure with the formula II or a pharmaceutically acceptable salt thereof.

Specific compounds of the disclosure are such derivatives described in U.S. Pat. No. 5,532,259, in the international patent application WO 91/717748 and in Kuo et al., (Kuo et al., 1996), each of which is incorporated herein by reference.

In Kuo et al., (Kuo et al., 1996) examples for the preparation of compounds according to the present description is shown, each of which is incorporated herein by reference.

Furthermore, compounds according to the disclosure can either be commercially purchased or prepared according to the methods described in the publications, patents or patent publications disclosed herein. Further, optically pure compositions can be asymmetrically synthesized or resolved using known resolving agents or chiral columns as well as other standard synthetic organic chemistry techniques. Compounds used in the disclosure may include compounds that are racemic, stereomerically enriched or stereomerically pure, and pharmaceutically acceptable salts, solvates, stereoisomers, and prodrugs thereof.

For example, FK778 can be manufactured according to methods described in the U.S. Pat. No. 3,308,865 (see example 14). The FK778 may include a conformer and a stereoisomer (see Kobayashi et al.). As used herein, when "FK778" is specified, it is to be understood that such conformers and isomers also included within the scope of this disclosure. Also, FK778 can be in another tautomer form, and such a tautomer form is also included within the scope of this disclosure. For example, FK778 can be either in its enol or keto form, i.e. 2-cyano-3-oxo-N-[4-(trifluoromethyl)phenyl]-6-heptynamide, as shown in Kobayashi et al. For the use according to the present disclosure, FK778 can be in a solvate, which is included within the scope of the present disclosure. The solvate preferably includes a hydrate and an ethanolate.

Preferred compounds used according to the disclosure are small organic molecules having a molecular weight less than about 1,000 g/mol, and are not proteins, peptides, oligonucleotides, oligosaccharides or other macromolecules.

In advantageous embodiments, the compounds used in the treatment of neuropathic pain according to the present disclosure are administered to the patient after a damage of the nervous system. Preferably, HR325 or FK778 is administered to the patient after a damage of the nervous system.

Surprisingly, the inventors have found that early-stage administration of a compound according to the disclosure, in particular of HR 325 or FK778, to mammalians with neuropathic pain, minimalize the pain and the analgesic effect is maintained for several weeks to months, also without further administration of the compound (see FIG. 1).

Figure 2:
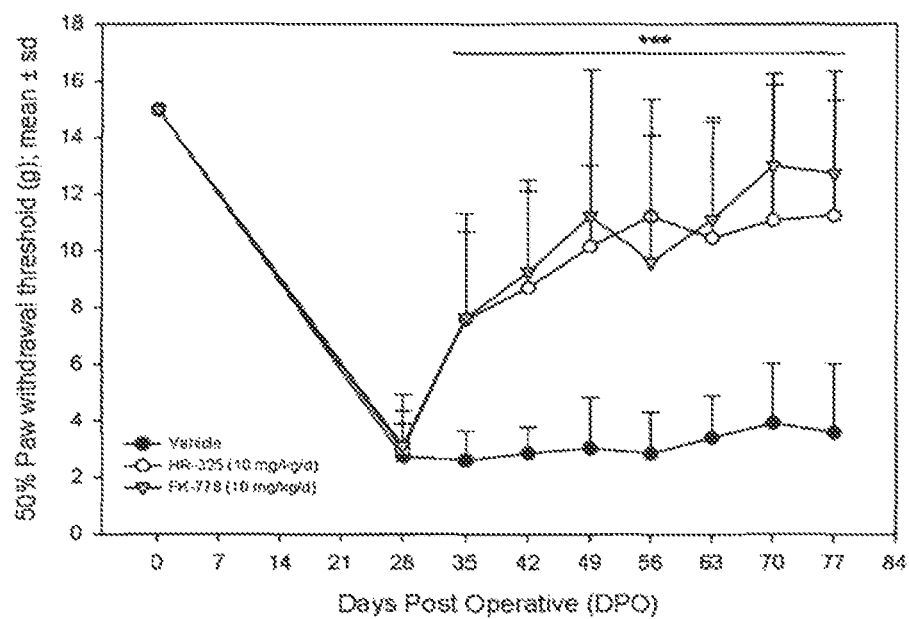
FIG. 2 shows the 50% paw withdrawal threshold (g) after contusion and oral gavage of HR325, FK778 and vehicle.
Figure 4:
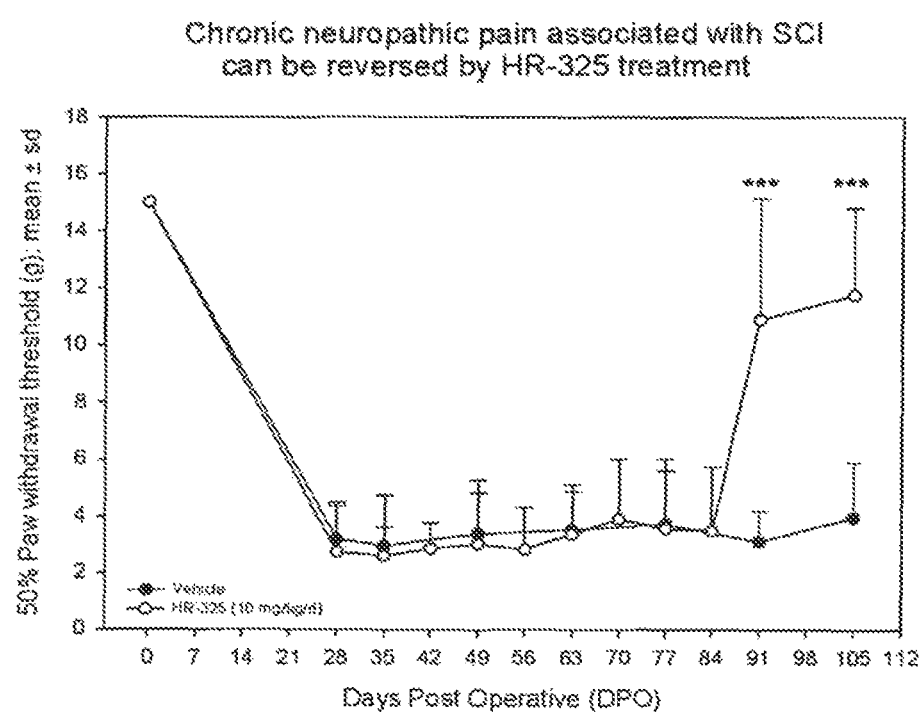
FIG. 4 shows the 50% paw withdrawal threshold (g) after contusion and oral gavage of HR325 and vehicle

Furthermore, the inventors have found that the administration of a compound according to the disclosure, in particular of HR 325 or FK-778, also minimize the neuropathic pain if the pain is already established (chronic pain). These results are shown in FIG. 2 and FIG. 4.

Neuropathic chronic pain according to the present disclosure may be a pain that persists for an extended period time, for example at least for more than one month. It can be a result of a long-term illness or a lingering result of an injury. An adequate definition for neuropathic chronic pain can be found at Bogduk, N; Merskey, H (1994). *Classification of chronic pain: descriptions of chronic pain syndromes and definitions of pain terms* (second ed.). Seattle: IASP Press. p. 212, which is hereby incorporated by reference.

In further advantageous embodiments, a compound according to the present disclosure is used as the only physically active compound in the treatment of neuropathic pain without a second active agent.

In yet other advantageous embodiments, the disclosure relates to pharmaceutical compositions for preventing and/or treating neuropathic pain, which comprises a therapeutically effective amount of a compound according to the present disclosure in admixture with a pharmaceutical acceptable carrier or excipient.

In advantageous embodiment, the pharmaceutical composition according to the present disclosure comprises a compound according to the present disclosure and no second active ingredient in the composition. In an advanced embodiment, laflunimus is used as the sole active agent for the treatment of neuropathic pain or neuropathic pain syndromes. In an advanced embodiment, laflunimus is used for the treatment of neuropathic pain without an immunomodulatory compound as a second active agent.

In advantageous embodiments, the pharmaceutical composition is used for preventing and/or treating, neuropathic pain, whereby the composition comprises a therapeutically effective amount of laflunimus or a physiologically functional derivative thereof in admixture with a pharmaceutical acceptable carrier or excipient in advantageous embodiments the pharmaceutical composition comprises a malononitrilamide selected from the group consisting of (1(3-methyl-4-trifluoro methylphenyl-carbamoyl)-2-cyclopropyl-2oxo-propionitrile), N-(4-trifluoromethyl)-phenyl-2-cyano-3-hydroxy-hept-2-en-6-in-carboxylic acidamide, and 2-cyano-3-cyclopropyl-3-oxo-(4-cyanophenyl)propionamide or a pharmaceutically acceptable salt, solvate, tautomer or stereoisomer thereof.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein, and unless otherwise specified, the term "solvate" means a compound of the present disclosure or a salt thereof that further includes a stoichiometric or non-stoichiometric amount of solvent hound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of compounds according to the present disclosure that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the disclosure that comprise —NO, —NO2, —ONO, or —ONO2 moieties. Prodrugs can typically be prepared using well-known methods, such as those described in Burger's Medicinal Chemistry and Drug Discovery, 172-178, 949-982 (Manfred E. Wolff ed., 5th ed. 1995% and Design of Prodrugs (H. Bundgaard ed., Elselvier, New York 1985). As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxymethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl end isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, [alpha]-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

As used herein, and unless otherwise specified, the term "stereoisomer" encompasses all enantiomerically/stereomerically pure and enatiomerically/stereomerically enriched compounds of this disclosure.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer, in certain cases, a compound of the disclosure is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this disclosure (e.g., R/S=30/70, 35/65, 40/60, 45/55, 55/45, 60/40, 65/35 and 70/30). Various inhibitor compounds of the present disclosure contain one or more chiral centers, and can exist as racemic mixtures of enantiomers or mixtures of diastereomers. This disclosure encompasses the use of stereomerically pure forms of such compounds, as well as the use of mixtures of those forms. For example, mixtures comprising equal or unequal amounts of the enantiomers of a particular inhibitor compound of the disclosure may be used in methods and compositions of the disclosure. These isomers may be asymmetrically synthesized or resolved using standard techniques such as chiral columns or chiral resolving agents. See, e.g., Jacques, J., et al, Enantiomers, Racemates and Resolutions (Wiley-Interscience, New York, 1981); Wilen, S. H., et al, Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

As used herein, and unless otherwise indicated, the term "tautomers" means isomers of a compound according to the present disclosure that readily interconverts by tautomerization. This reaction commonly results in the formal migration of a hydrogen atom or proton, accompanied by a switch of a single bond and adjacent double bond. Common tautomeric pairs are ketone-enol, ketone-ynol, amide-imidic acid, lactam-lactim, an amide-imidic acid tautomerism in heterocyclic rings, enamine-imine, enamine-enamine, and anomers of reducing sugars in solution interconvert through an intermediate open chain form.

For example, in an advantageous embodiment the compound having formula II (FK778) can be either in its enol (FK778) or keto form, i.e. 2-cyano-3-oxo-N-[4-(trifluoromethyl) phenyl]-6-heptynamide and such a tautomer form is also included within the scope of this disclosure.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives am prodrugs such as those described below in the present application.

The term "derivative" as used herein refers to a compound that is derived from a similar compound or a compound that can be imagined to arise from another compound, if one atom is replaced with another atom or group of atoms. The term "derivative" as used herein refers also to a compound that at least theoretically can be formed fan the precursor compound (see Oxford Dictionary of Biochemistry and Molecular Biology. Oxford University Press. ISBN 0-19-850673-2.) In advantageous embodiment of the present disclosure the term "derivative" is used for derivatives from laflunimus.

The disclosure is also directed to the use of compounds of the formula I, II, III, IV or of formula V and of their pharmacologically tolerable salts or physiologically functional derivatives for the production of a medicament for the prevention and treatment of neuropathic pain and neuropathic pain syndromes.

Methods and uses according to the present disclosure encompass methods of preventing, treating and/or managing neuropathic pain and related syndromes, but are not limited to, postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., postmastectomy syndrome, postthoracotomy syndrome, phantom pain), and complex regional pain syndrome (reflex sympathetic dystrophy and causalgia).

The symptoms, conditions and/or symptoms associated with neuropathic pain include, but are not limited to, dysesthesias (spontaneous or evoked burning pain, often with a superimposed lancinating component), but pain may also be deep and aching. Other sensations like; hyperesthesia, hyperalgesia, allodynia (pain due to a nonnoxious stimulus), and hyperpathia (particularly unpleasant, exaggerated pain response).

The suitability of a particular route of administration of an compound according to the present disclosure employed for a particular active agent will depend on the active agent itself (e.g., whether it can be administered orally without decomposing prior to entering the blood stream) and the disease being treated. An advantageous embodiment of the route of administration for a compound according to the present disclosure is orally. Further routes of administration are known to those of ordinary skill in the art.

The dosage of therapeutically effective amount of at least one compound varies from and also depends upon the age and condition of each individual patient to be treated. In an embodiment of the present disclosure, the recommended daily dose range of a compound according to the present disclosure for the conditions and disorders described herein lies within the range of from about, a daily dose of about 1 mg-1 g/body, preferable 5 mg-5 g/body and more preferable 10 mg-2 g/body of the active ingredient is generally given for treating this disease, and an average single dose of about 0.5-1 mg, 5 mg, 10 mg, 50 mg, 100 mg, 250 mg, 500 mg, 1 g, 2 g and 3 g is generally administered. Daily dose for administration in humans for treating this disease (neuropathic pain or neuropathic pairs syndromes) could be in the range of about 0.1-50 mg/kg.

While the term for administering of at least one compound to prevent this disease (neuropathic pain or neuropathic pain syndromes) varies depending on species, and the nature and severity of the condition to be prevented, the compound may usually be administered to humans for a short term or a long term, i.e. for 1 week to 1 year.

Pharmaceutical compositions can be used in the preparation of individual, single unit dosage forms. The compounds of the present disclosure can be used in the form of pharmaceuticals compositions, for example, in solid, semisolid or liquid form, which contains one or more of the compounds according to the present disclosure as active ingredient associated with pharmaceutically acceptable carriers or excipient suitable for oral, parenteral such as intravenous, intramuscular, intrathecal, subcutaneous, enteral, intrarectal or intranasal administration. The active ingredient may be compounded, for example, with the usual non-toxic, pharmaceutically acceptable carriers for tablets, pellets, capsules, suppositories, solutions (saline for example), emulsion, suspensions (olive oil, for example), ointment and any other form suitable for use. The carriers which can be used are water, glucose, lactose gum acacia, gelatine, mannitol, starch paste, magnesium trisilicate, corn starch, keratin, colloidal silica, potato starch, urea and other carriers suitable for use in manufacturing preparations, in solid, semisolid or liquid form, and in addition auxiliary, stabilizing, thickening and colouring agents and perfumes may be used. The active object compound is included in the pharmaceutical composition in art effective amount sufficient to prevent and/or treat the disease.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the disclosure will typically vary depending on their use. For example, a dosage form used in the acute treatment of a disease may contain larger amounts of one or more of the active agents it comprises than a dosage form used in the chronic treatment of the same disease. Similarly, a parenteral dosage form may contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active agents in the dosage form. For example, the decomposition of some active agents may be accelerated fey some excipients such as lactose, or when exposed to water. Active agents that comprise primary or secondary amines are particularly susceptible to such accelerated decomposition. Consequently, this disclosure encompasses pharmaceutical compositions and dosage forms that contain little, if any, lactose or other mono- or di-saccharides. As used herein, the term "lactose-free" means that the amount of lactose present, if any, is insufficient to substantially increase tie degradation rate of an active ingredient.

Lactose-free compositions of the disclosure can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, hut are not limited to, hermetically sealed foils, plastics, unit dose containers (e.g. vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or sail buffers.

Like the amounts and types of excipients, the amounts and specific types of active agents in a dosage form may differ depending on factors such as, but not limited to, the route by which it is to be administered to patients. However, typical dosage forms of the disclosure comprise a compound according to the present disclosure or a pharmaceutically acceptable salt, solvate, hydrate, stereoisomer, clathrate, or prodrug thereof in an amount of from about 0.10 to about 150 mg. Typical dosage forms comprise a compound according to the present disclosure or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione in an amount of about 1, 2, 5, 10, 25 or 50 mg. In a specific embodiment, a preferred dosage form comprises 3-(4-amino-1-oxo-1,3-dihydro-isoindol-2-yl)-piperidine-2,6-dione in an amount of about 5, 10, 25 or 50 mg.

Oral Dosage Forms of pharmaceutical compositions of the disclosure that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the disclosure are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, hut are not limited to, starches, sugars, micro-crystal line cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose, acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the disclosure. The amount of disintegrate used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrates that can be used in pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.), CAS-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the disclosure comprises a compound of the disclosure, anhydrous lactose, microcrystalline cellulose, polyvinylpyrrolidone, stearic acid, colloidal anhydrous silica, and gelatin.

Active ingredients of the disclosure can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein can be readily selected for use with the active ingredients of the disclosure. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the disclosure are well known to those skilled in the art. Examples include, but are not limited to: Water for injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the disclosure. For example, cyclodextrin and its derivatives can be used to increase the solubility of a compound of the disclosure and its derivatives. See, e.g., U.S. Pat. No. 3,134,127, which is incorporated herein by reference.

Topical and mucosal dosage forms of the disclosure include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g. carriers and diluents) and other materials that can be used to provide topical and mucosal dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Typically, active ingredients of the disclosure are preferably not administered to a patient at the same time or by the same route of administration. This disclosure therefore encompasses kits which, when used by the medical practitioner, can simplify the administration of appropriate amounts of active ingredients to a patient.

A typical kit of the disclosure comprises a dosage form of a compound of the disclosure, or a pharmaceutically acceptable salt, solvate, hydrate, stereoisomer, prodrug, or clathrate thereof. Kits encompassed by this disclosure can further comprise additional active agents. Examples of the additional active agents include, but are not limited to, those disclosed herein (see, e.g., section 4.2). Kits of the disclosure can further comprise devices that are used to administer the active ingredients. Examples of such devices include, but are not limited to, syringes, drip bags, patches, and inhalers. In an advantageous embodiment, a kit of the disclosure contains, laflunimus and no additional immunomodulatory compound.

Kits of the disclosure can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Advantageous examples for compounds according to the present disclosure for the use in the treatment of neuropathic pain:
A) HR325 (Laflunimus) (1(3-methyl-4-trifluoro methyl-phenyl-carbamoyl)-2-cyclopropyl-2oxo-propionitrile)
B) FK778 (N-(4-trifluoromethyl)-phenyl-2-cyano-3-hydroxy-hept-2-en-6-in-carboxylic acidamide)
C) MNA279 (2-cyano-3-cyclopropyl-3-oxo-(4-cyanophenyl)propionamide)
D) 5-(3-butynyl)-N-[4-(trifluoromethyl) phenyl]-4-isoxazolecarboxamide The following examples and methods are offered for illustrative purposes only, and are not intended to limit the scope of the present disclosure in any way.

METHODS AND EXAMPLES

A series of non-clinical pharmacology and toxicology studies have been performed to support the clinical evaluation of the compounds according to the present disclosure in human subjects. These studies were performed in accordance with internationally recognized guidelines for study design and in compliance with the requirements of Good Laboratory Practice (GLP) unless otherwise noted.

Example 1

Laflunimus (HR325) treatment to suppress the development of mechanical allodynia after severe spinal cord contusion injury in the rat.

Surgical Methods

Thirteen week-old female Lewis rats (Charles River, Sulzfeld Germany) were housed under a 12:12 h dark/light regime and allowed free access to water and food. After one week of habituation the animals underwent general anesthesia with a mixture of isoflurane and air (induction: 5% isoflurane, maintenance: 2.2% isofluorane). A Th10 laminectomy was performed without rupturing the dura and a severe contusive SCI (25 gcm NYU/MASCIS II impactor) (Gruner, 1992 #3) was induced. After suturing muscle and skin, a subcutaneous (s.c.) injection of 5 ml of Ringers Lactate was given. Bladders were emptied manually 2 times a day until spontaneous voiding returned (usually within 1 week). The lesion severity was verified by the impact velocity and contusion depth of the impactor rod. Animals with an impact velocity error >5% were excluded from further analysis. After injury, individual rats were randomly assigned into a treatment group. The following groups were used:

Group 1: SCI+ vehicle (1.5% CMC in sterile water) by gavage for 7 days, from DPO 1 till DPO 7

Group 2: SCI+HR 325 (10 mg/kg/day) in vehicle by gavage for 7 days, from DPO 1 till DPO 7

Group 3: SCI+HR 325 (20 mg/kg/day) in vehicle by gavage for 7 days, from DPO 1 till DPO 7

Group 4: SCI+HR 325 (30 mg/kg/day) to vehicle by gavage for 7 days, from DPO 1 till DPO 7

Assessment of Mechanical Sensitivity:

The mechanical sensitivity response was measured as the direct pressure stimulus required eliciting foot withdrawal in nonrestrained conditions. All tests were conducted in the morning between 7:30 and 10:30 am and the person performing the behavioral tests was blinded to the experimental groups. Animals were habituated to the testing apparatus for at least 20 min before testing. Each animal was subjected to the stimulation of a series of von Frey filaments ranging from 0.4 to 15 g (log force 3.61, 3.84, 4.08, 4.31, 4.56, 4.74, 4.93 and 5.18) using the Up-Down paradigm according to Chaplan (Chaplan et al., 1994). The selected von Frey filament was pressed against the plantar surface of the hind paw to the point of 30° bending for 3 s. Paw withdrawal response was considered as the positive response. The 50% threshold force needed for paw withdrawal was calculated for both hind paws of each rat and the mean value of both hind paws was used to represent the mechanical sensitivity of this animal.

Results:

Mechanical Sensitivity

The mechanical sensitivity (indicated by the 50% threshold force for paw withdrawals) was determined by the Up-Down method using von Frey filaments. All rats were baseline tested before surgery and tested again on day 28 post surgery, because this is the first time point at which all rats cart sit with the hind paws in plantar position. At baseline all animals reached the maximal 50% threshold force of 15 g, as consequence there were no differences between the two groups. As expected, both the vehicle treated as well as the HR-325 treated animals showed mechanical hypersensitivity at DPO 28. However, as consequence of the HR-325 treatment the mechanical hypersensitivity was significantly reduced in all HR-325 treated dosage groups at DPO 28 (one-way ANOVA; $F_{3,53}=19.93$ $p<0.001$, see FIG. 1). This statistically significant difference between the treated animals and the vehicle controls remained till the end of the experiment at DPO 63 (one-way ANOVA; $F_{3,53}=35.34$ $p<0.001$, see FIG. 1). Thus, all tested HR-325 dosages (i.e. 10, 20 and 30 mg/kg/d) are able to suppress the development of mechanical allodynia after experimental spinal cord injury (see FIG. 1).

Example 2

HR325 and FK778 treatment can both reverse central neuropathic pain induced by severe spinal cord contusion injury in the rat.

Surgical Methods

For surgical methods see example 1.

After injury, individual rats were randomly assigned into a treatment group. The following groups were used:

Group 1: SCI+ vehicle (1.5% CMC in sterile water) by gavage for 7 days, from DPO 28 till DPO 35

Group 2: SCI+HR 325 (10 mg/kg/day) in vehicle by gavage for 7 days, from DPO 28 till DPO 35

Group 3: SCI+FK 778 (10 mg/kg/day) in vehicle by gavage for 7 day, from DPO 28 till DPO 35

Assessment of Mechanical Sensitivity:

For the assessment of mechanical sensitivity see example 1.

The Acetone Test:

A slightly modified method of De la Calle and colleagues (De la Calle et al., 2002) was used for the determination of the reactivity to a cold chemical stimulus. The rat was placed in acrylic cages on top of a wire mesh grid, which allowed access to the paws, and acetone was applied to the plantar surface of the hind paw. To do this, 100 µl of acetone was sprayed onto the plantar surface of the rat's hind leg from below the grid with a syringe holding 2.5 ml. The time spent with the leg withdrawn from floor during the 60 s following exposure to acetone was recorded. Both hind legs were tested in each animal with an interval of 5-10 min between each test. The average reaction time between the two legs was taken for further analysis. A minimal value of 1 s was assigned to convey a fast or brisk reaction, while 0 was assigned if there was no reaction at all. This acetone test has been described as composing of cold, chemical, and possibly mechanical stimulation.

Results:

Mechanical Sensitivity

The mechanical sensitivity (indicated by the 50% threshold force for paw withdrawals) was determined by the Up-Down method using von Frey filaments. All rats were baseline tested before surgery and tested again on day 28 post surgery, because this is the first time point at which all rats can sit with the hind paws in plantar position. At baseline all animals reached the maximal 50% threshold force of 15 g, as consequence there were no differences between the two groups. As expected, all animate showed severe mechanical hypersensitivity at DPO 28, the withdrawal threshold dropped from 15 grams before injury to 2.7, 3.0 and 3.1 grams in vehicle control animals, HR-325 treated animals and FK-778 treated animals, respectively. Then from DPO 28 till DPO 35 we started the oral treatment with HR-325, FK-778 or vehicle which tremendously affected the mechanical hypersensitivity. At DPO 35 the withdrawal threshold was significantly higher in both HR-325 and FK-778 treated animals when compared to vehicle control animals (one-way ANOVA; $F_{2,35}=12.6$ $p<0.001$, see FIG. 2). This statistically significant difference between the treated animals and the vehicle controls remained till the end of the experiment at DPO 77 (one-way ANOVA; $F_{2,35}=24.2$ $p<0.001$, see FIG. 2). Thus, HR-325 and FK-778 are both able to reverse mechanical allodynia after experimental spinal cord injury.

The Acetone Test

Figure 3:
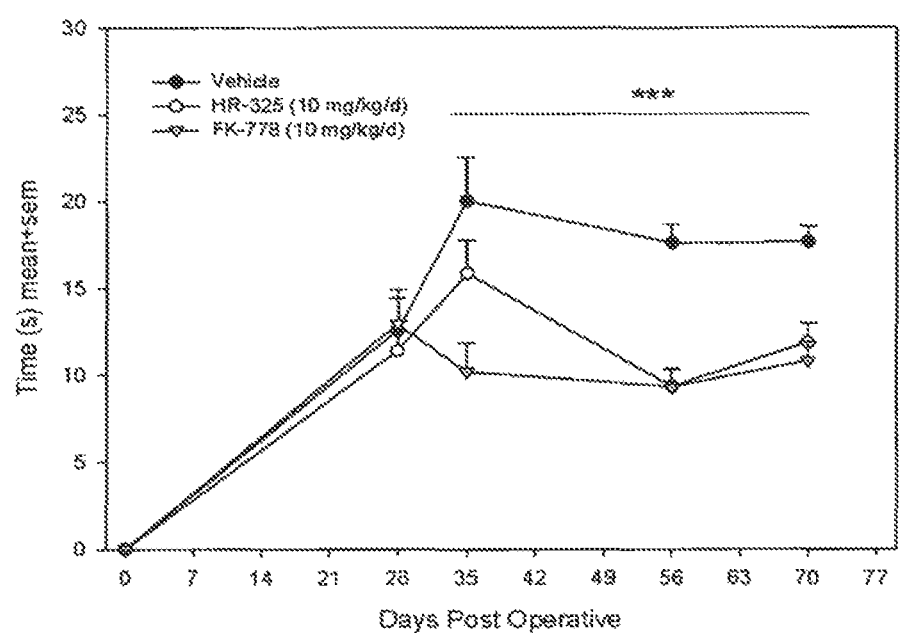
FIG. 3 shows the duration (s) of reactivity to acetone applied to the plantar surface of the hindpaw.

The acetone test was used for the determination of the reactivity to a cold chemical stimulus. The obtained results show clearly that before injury the acetone does not evoke any reaction at all when applied to the plantar surface of the hind paws. However, at DPO 28 all animals showed a clear reaction to the acetone exposure. The following 7 days up to DPO 35 the treatment started with either HR-325, FK-778 or vehicle. As a consequence of the treatment the first significant differences between the treatment groups became obvious at DPO 35. The FK-778 treated animals responded significantly shorter to the acetone exposure than the vehicle controls (one-way ANOVA; $F_{2,34}=5.6$ p<0.01, see FIG. 3). Three weeks later at DPO 56 there was still a marked difference between the groups (one-way ANOVA; $F_{2,34}=21.0$ p<0.001, see FIG. 3), a Bonferroni post-hoc test revealed that both FK-778 and HR-325 treated animals responded significantly shorter to the acetone exposure than the vehicle controls. These differences remained unchanged till the end of the experiment at DPO 70 (one-way ANOVA; $F_{2,34}=12.3$ p<0.01, see FIG. 3), Thus, HR-325 and FK-778 are both able to reverse cold allodynia after experimental spinal cord injury.

Example 3

Figure 5:
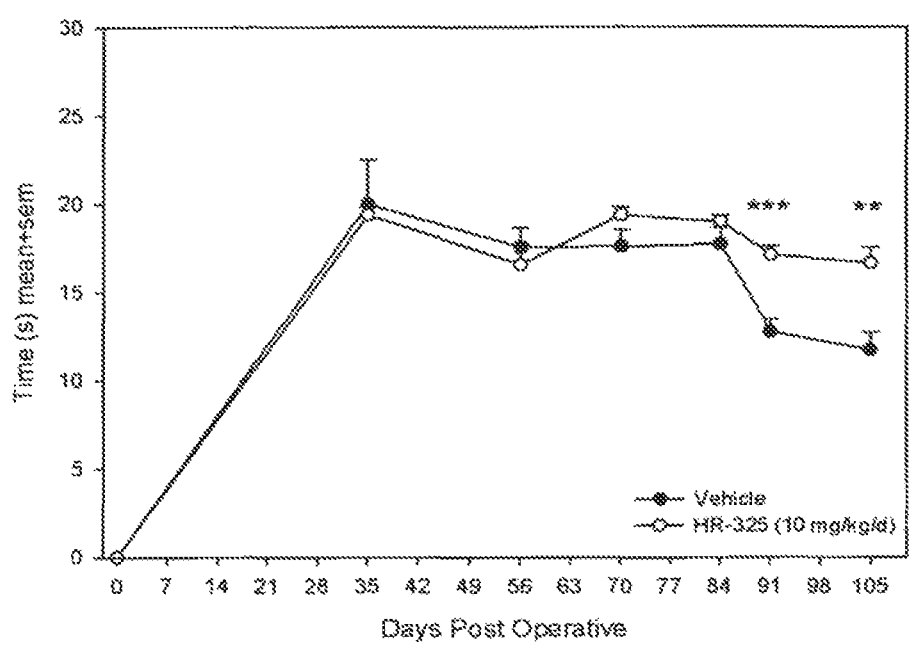
FIG. 5 shows the duration (s) of reactivity to acetone applied to the plantar surface of the hindpaw.

HR325 treatment can reverse chronic central neuropathic pain three months after spinal cord contusion injury.
Surgical Methods
For surgical methods see example 1.
After injury, individual rats were randomly assigned into a treatment group. The following groups were used:
Group 1: SCI+ vehicle (1.5% CMC in sterile water) by gavage for 7 days, from DPO 84 till DPO 91
Group 2: SCI+HR 325 (10 mg/kg/day) in vehicle by gavage for 7 days, from DPO 84 till DPO 91
Assessment of Mechanical Sensitivity:
For the assessment of mechanical sensitivity see example 1.
The Acetone Test:
For the assessment of mechanical sensitivity see example 2.
Results:
Mechanical Sensitivity
The mechanical sensitivity (indicated by the 50% threshold force for paw withdrawals) was determined by the Up-Down method using von Frey filaments. All rats were baseline tested before surgery and tested again on day 28 post surgery, because this is the first time point at which all rats can sit with the hind paws in plantar position. At baseline all animals reached the maximal 50% threshold force of 15 g, as consequence there were no differences between the two groups. As expected, all animals showed severe mechanical hypersensitivity at DPO 28, the withdrawal threshold dropped from 15 grams before injury to 3.2 and 2.7 grams in vehicle control animals and HR-325 treated animals, respectively. Thereafter the 50% threshold force remained stable for the next two months up to DPO 84 at which the oral treatment with either HR-325 or vehicle was started. As a consequence of this 7 days treatment the 50% threshold force increased, at DPO 91 the withdrawal threshold was significantly higher in HR-325 treated animals when compared to vehicle control animals (Student T-test; t=5.33 p<0.001, see FIG. 4). A comparable difference between the groups was noted at the end of the experiment at DPO 105 (Student T-test; t=7.68 p<0.00% see FIG. 4). Thus, HR-325 can reverse a chronic mechanical allodynia caused by spinal cord trauma even alter lasting 3 months.
The Acetone Test
The acetone test was used for the determination of the reactivity to a cold chemical stimulus. The obtained results show clearly that before injury the acetone does not evoke any reaction at all when applied to the plantar surface of the hind paws. However, at DPO 35 all animals showed a clear reaction to the acetone exposure. The following 2 months up to DPO 84 the reaction to the acetone exposure remained unchanged. However, at DPO 84 the 7 days oral treatment started with either HR-325 or vehicle. As a consequence of the treatment the first significant differences between the two groups became obvious at DPO 91 (Student T-test; t=4.70 p<0.001, see FIG. 5). A comparable difference between the groups was noted at the end of the experiment at DPO 105 (Student T-test; t=3.54 p<0.01, see FIG. 5). Thus, HR-325 can reverse a chronic cold allodynia caused by spinal cord trauma even after lasting 3 months.

Altogether, the data presented in these examples clearly demonstrate that, HR-325 treatment (i.e. 10, 20 and 30 mg/kg/d) can suppress the development of mechanical allodynia after spinal cord trauma. Moreover, Laflunimus (HR-325) and FK-778 treatment are able to reverse both mechanical- and thermal allodynia after spinal cord injury. Finally, HR-325 treatment can reverse spinal cord trauma indiced mechanical- and cold allodynia that is ongoing for 3 months.

Example 4

HR325 treatment can attenuate peripheral neuropathic pain after chronic constriction injury (CCI) of the sciatic nerve.
Surgical Methods
Surgery was performed according to the methods of Bennett and Xie (1988). The common sciatic nerve was exposed at the level of the middle of the thigh by blunt dissection through the biceps femoris. Proximal to the sciatic trifurcation, about 7 mm of nerve was freed of adhering tissue, and tour ligatures (5.0 chromic catgut) were tied loosely around the nerve with about 1-mm spacing. Great care was taken to tie the ligatures, such that the diameter of the nerve was seen to be just barely constricted. This constriction of the nerve leads to intraneural oedema, focal ischemia, and an axonal degeneration. As a consequence, this model results in cold and mechanical allodynia, and some symptoms of spontaneous pain which lasts for a period of more than 2 months (Attal et al., 1990; Bennett and Xie, 1988)
Fourteen days (DPO 14) alter injury, all individual rats were treated daily with HR-325 for 7 days up to DPO 21.
Assessment of mechanical Sensitivity:
The mechanical sensitivity response was measured as the direct pressure stimulus required eliciting foot withdrawal in nonrestained conditions. Animals were habituated to the testing apparatus for at least 20 min before testing. Each animal was subjected to the stimulation of a series of von Frey filaments ranging from 1.0 to 60 g using the Up-Down paradigm according to Chapter (Chaplan et al., 1994). The selected von Frey filament was pressed against the plantar surface of the hind paw to the point of 30° bending for 3 s. Paw withdrawal response was considered as the positive response. The 50% threshold force needed for paw withdrawal was calculated for both hind paws of each rat.
The Acetone Test
A slightly modified method of De la Calle and colleagues (De la Calle et al., 2002) was used for the determination of the reactivity to a cold chemical stimulus. The rat was placed in acrylic cages on top of a wire mesh grid, which allowed access to the paws, and acetone was applied to the plantar surface of the hind paw. To do this, 100 µl of acetone was sprayed onto the plantar surface of the rat's hind leg front below the grid with a syringe holding 2.5 ml. The time spent with the leg withdrawn from floor during the 60 s following exposure to acetone was recorded, Both, hind legs were, tested in each animal with an interval of 5-10 min between each test.

Results:

Mechanical Sensitivity

Figure 6:
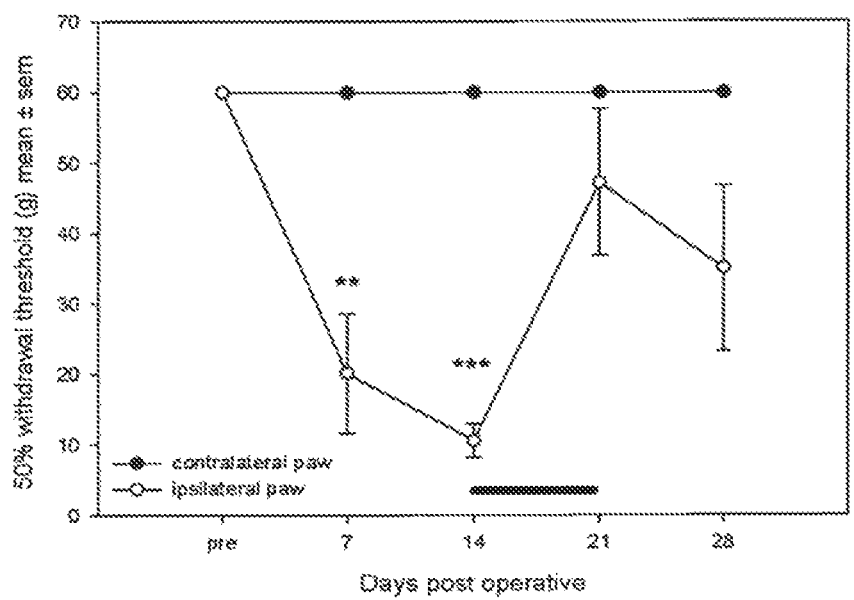
FIG. 6 shows the 50% paw withdrawal threshold (g) after constriction of the sciatic nerve and oral gavage of HR325

The mechanical sensitivity (indicated by the 50% threshold force for paw withdrawals) was determined by the Up-Down method using von Frey filaments. All rats were baseline tested before surgery and tested again on day 7 and 14 post surgery. At baseline all animals reached the maximal 30% threshold force of 60 g in both the contra- and ipsilateral paw. As expected, all animals showed severe mechanical hypersensitivity in the ipsilateral paw at DPO 7 and DPO 14. The withdrawal threshold dropped from 60 grams before injury to 10 grams 14 days after injury, which was significantly lower when compared to the contralateral paw. Then from DPO 14 till DPO 21 the oral treatment with HR-325 (black bar; FIG. 6) was givers. At DPO 21 the withdrawal threshold in the ipsilateral paw significantly increased up to 47 grains, which was not significantly different from the contralateral paw (T-test; n.s., see FIG. 6). One week later at DPO 28 the treatment affect of HR-325 remained stable since the withdrawal threshold in the ipsilateral paw was still comparable with the contralateral paw.

The Acetone Test

Figure 7:
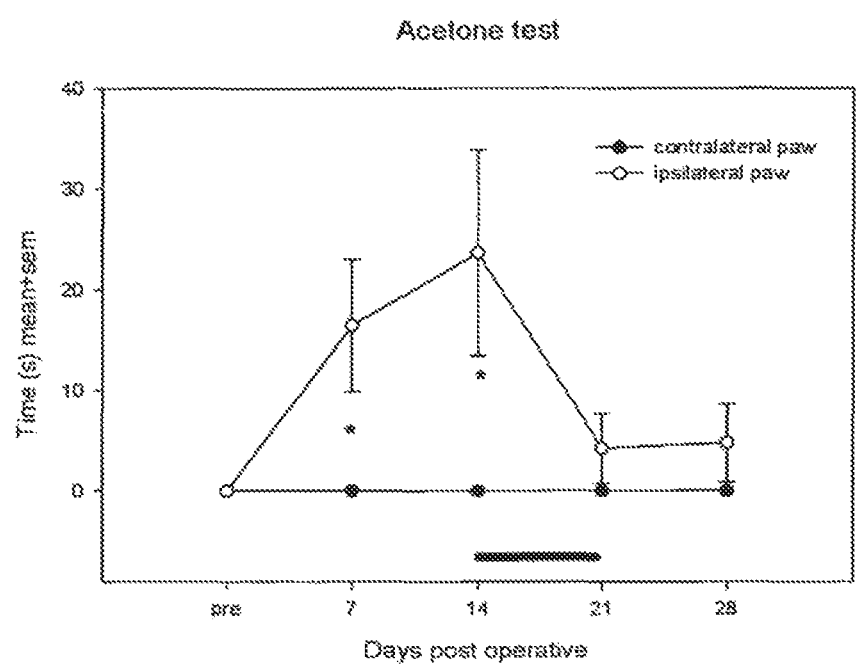
FIG. 7 shows the duration (s) of reactivity to acetone applied to the plantar surface of the hind paws after constriction of the sciatic nerve and oral gavage of HR325

The acetone test was used for the determination of the reactivity to a cold chemical stimulus. The obtained results show clearly that before injury the acetone does not evoke any reaction at all when applied to the plantar surface of the hind paws. However, at DPO 7 and DPO 14 most animals showed a clear reaction to the acetone exposure in the ipsilateral paw, an average reaction time of 16 and 23 seconds respectively. Since the contralateral paw did not react at all a statistically significant difference was noted between the two hind paws. The following 7 days up to DPO 21 the animals were treated with daily 10 mg/kg HR-325 (black bar; FIG. 7). As a consequence of the treatment the reactivity to the acetone almost diminished in the ipsilateral paw. One week later at DPO 28 the reactivity to the acetone exposure was still very low and comparable to the reactivity in the contralateral paw (T-test; n.s., see FIG. 7).

Example 5

HR325 treatment can attenuate peripheral neuropathic pain alter partial ligation of the sciatic nerve.

Surgical Methods

The methods of Seltzer et al. (1990) were followed. The dorsum of the sciatic nerve was carefully freed from surrounding connective tissues at a site near the trochanter just distal to the point at which the posterior biceps semitendinosus nerve branches off the common sciatic nerve. The nerve was fixed in its place by pinching the epineurium on its dorsal aspect, taking care not to press the nerve against underlying structures. An 8-0 (Polyamide 6) suture was inserted into the nerve and tightly ligated so that the dorsal ⅓-½ of the nerve thickness was trapped in the ligature (Seltzer et al., 1990).

Fourteen days up to (DPO 14) after injury, all individual rats were treated daily with HR-325 for 7 days up to DPO 21.

Assessment of Mechanical Sensitivity:

For the assessment of mechanical sensitivity see example 4.

The Acetone Test

For the assessment of mechanical sensitivity see example 4.

Results:

Mechanical Sensitivity

Figure 8:
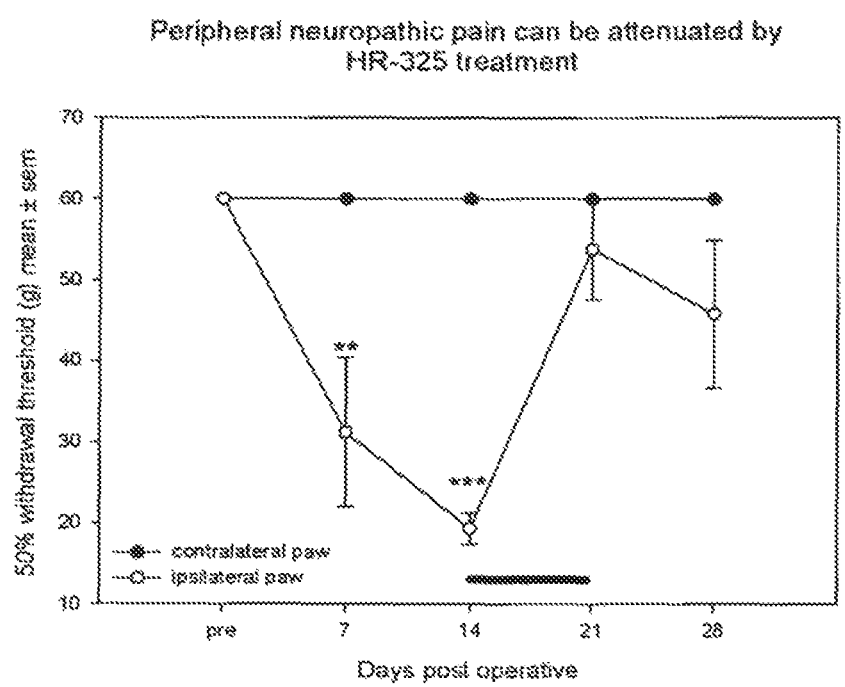
FIG. 8 shows the 58% paw withdrawal threshold (g) after partial ligation of the sciatic nerve and oral savage of HR325

The mechanical sensitivity (indicated by the 50% threshold force for paw withdrawals) was determined by the Up-Down method using von Frey filaments. All rats were baseline tested before surgery and tested again on day 7 and 14 post surgery. At baseline all animals reached the maximal 50% threshold force of 60 g in both the contra- and ipsilateral paw. As expected, all animals showed severe mechanical hypersensitivity in the ipsilateral paw at DPO 7 and DPO 14. The withdrawal threshold dropped from 60 grams before injury to 19 grams 14 days after injury, which was significantly lower when compared to the contralateral paw. Then from DPO 14 till DPO 21 the oral treatment with HR-325 (black bar; FIG. 8) was given. At DPO 21 the withdrawal threshold in the ipsilateral paw significantly increased up to 54 grams, which was not significantly different from the contralateral paw (T-test; n.s., see FIG. 8). One week later at DPO 28 the treatment affect of HR-325 remained stable since the withdrawal threshold in the ipsilateral paw was still comparable with the contralateral paw.

The Acetone Test

Figure 9:
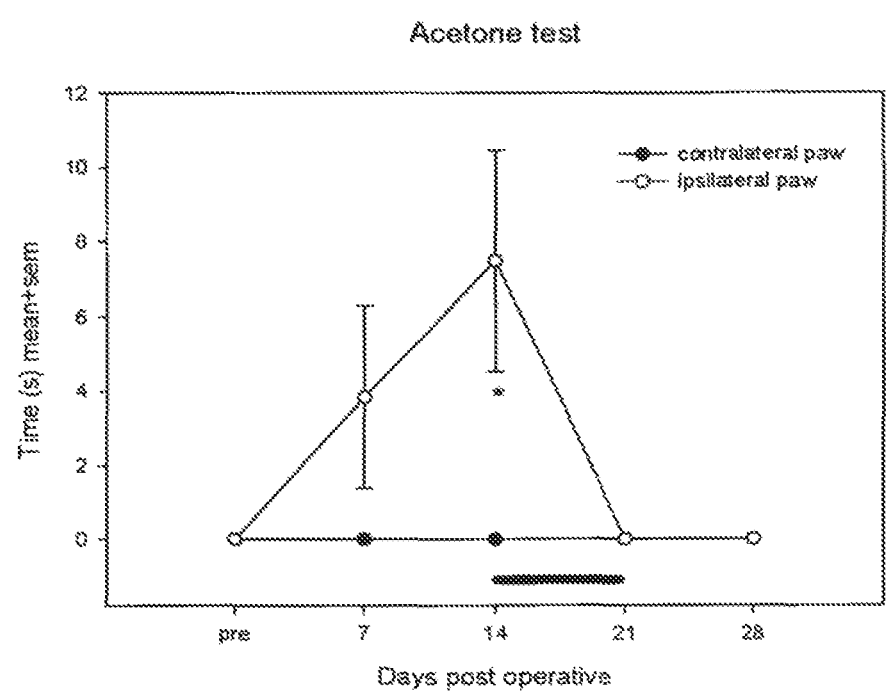
FIG. 9 shows the duration (s) of reactivity to acetone applied to the plantar surface of the hind paws after partial ligation of the sciatic nerve and oral gavage of HR325

The acetone test was used for the determination of the reactivity to a cold chemical stimulus. The obtained results show clearly that before injury the acetone does not evoke any reaction at ail when applied to the planter surface of the hind paws. However, at DPO 7 and DPO 14 most animals showed a clear reaction to the acetone exposure in the ipsilateral paw, an average reaction time of 4 and 8 seconds respectively. Since the contralateral paw did not react at all a statistically significant difference was noted between the two hind paws. The following 7 days up to DPO 21 the animals were treated with dally 10 mg/kg HR-325 (black bar; FIG. 9). As a consequence of the treatment the reactivity to the acetone completely diminished in the ipsilateral paw. One week later at DPO 28 the animals did still not show any reactivity to the acetone exposure Thus, the cold chemical stimulus was not painful anymore (see FIG. 9).

The results show that a controlled pharmacotherapy by malononitrilamides can be used for treating neuropathic pain and neuropathic pain syndromes.

The embodiments of the disclosure described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

ADDITIONAL REFERENCES

The following additional publications are incorporated herein by references:

Afridi, S., Goadsby, P. J., 2003. New onset migraine with a brain stem cavernous angioma. J Neurol Neurosurg Psychiatry. 74, 680-2.

Attal, N., et al., 1990. The bidirectional dose-dependent effect of systemic naloxone is also related to the intensity and duration of pain-related disorders: a study in a rat model of peripheral mononeuropathy. Brain Res. 525, 170-4.

Bennett, G. J., Xie, Y. K., 1988. A peripheral mononeuropathy in rat that produces disorders of pain sensation like those seen in man. Pain. 33, 87-107.

Cao, L., DeLeo, J. A., 2008. CNS-infiltrating CD4+ T lymphocytes contribute to murine spinal nerve transection-induced neuropathic pain. Eur J Immunol. 38, 448-58.

Chaplan, S. R., et al., 1994. Quantitative assessment of tactile allodynia in the rat paw. J Neurosci Methods. 53, 55-63.

Costigan, M., et al., 2009. T-cell infiltration and signaling in the adult dorsal spinal cord is a major contributor to neuropathic pain-like hypersensitivity. J Neurosci. 29, 14415-22.

Davis, J. P., et al., 1996. The immunosuppressive metabolite of leflunomide is a potent inhibitor of human dihydroorotate dehydrogenase. Biochemistry. 35, 1270-3.

De la Calle, J. L., et al., 2002. Intrathecal transplantation of neuroblastoma cells decreases heat hyperalgesia and cold allodynia in a rat model of neuropathic pain. Brain Res Bull. 59, 205-11.

Goadsby, P. J., 2002. Neurovascular headache and a midbrain vascular malformation: evidence for a role of the brainstem in chronic migraine. Cephalalgia. 22, 107-11.

Greene, S., et al., 1995. Inhibition of dihydroorotate dehydrogenase by the immunosuppressive agent leflunomide. Biochem Pharmacol. 50, 861-7.

Kuo, E. A., et al., 1996. Synthesis, structure-activity relationships, and pharmacokinetic properties of dihydroorotate dehydrogenase inhibitors: 2-cyano-3-cyclopropyl-3-hydroxy-N-[3'-methyl-4'-(trifluoromethyl)phenyl] propenamide and related compounds. J Med Chem. 39, 4608-21.

Seltzer, Z., et al., 1990. A novel behavioral model of neuropathic pain disorders produced in rats by partial sciatic nerve injury. Pain. 43, 205-18.

Williamson, R. A., et al., 1995. Dihydroorotate dehydrogenase is a high affinity binding protein for A77 1726 and mediator of a range of biological effects of the immunomodulatory compound. J Biol Chem. 270, 22467-72.

Zenonos, G., Kim, J. E., A T cell-orchestrated immune response in the adult dorsal spinal cord as a cause of neuropathic pain-like hypersensitivity after peripheral nerve damage: a door to novel therapies? Neurosurgery. 66, N24-5.

Zielinski, T., et al., 1995. Leflunomide, a reversible inhibitor of pyrimidine biosynthesis? Inflamm Res. 44 Suppl 2, S207-8.

In summary, examples of the present disclosure pertain:

to compounds for use in treating neuropathic pain and/or neuropathic pain syndrome, wherein the compounds are malononitrilamides.

to a compound that has the formula (I)

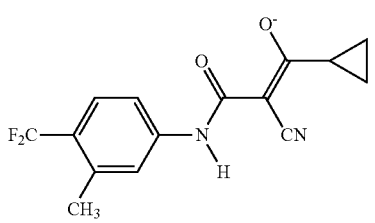

(I)

or derivatives or pharmaceutically acceptable salt, solvate, tautomer or stereoisomer thereof.

to derivative which are selected from the group consisting of:
i) (1(3-methyl-4-trifluoro methylphenyl-carbamoyl)-2-cyclopropyl-2oxo-propionitrile),
ii) N-(4-trifluoromethyl)-phenyl-2-cyano-3-hydroxy-hept-2-en-6-in-carboxylic acidamide,
iii) 2-cyano-3-cyclopropyl-3-oxo-(4-cyanophenyl)propionamide and
iv) 5-(3-butynyl)-N-[4-(trifluoromethyl) phenyl]-4-isoxazolecarboxamide and or a pharmaceutically acceptable salt, solvate, tautomer or stereoisomer thereof.

to derivative which are selected from the group consisting of the following compounds with the formula II to IV:

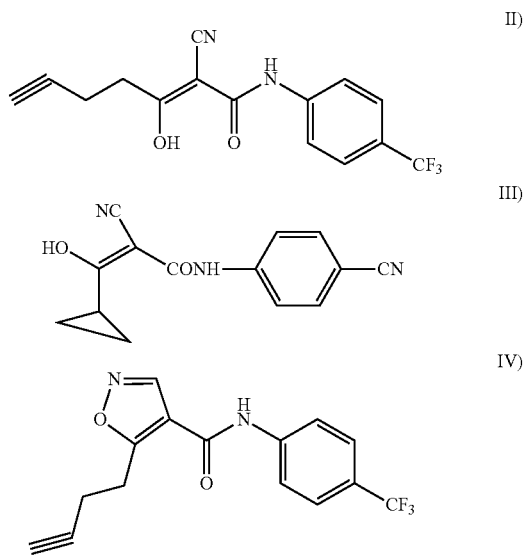

or a pharmaceutically acceptable salt, solvate, tautomer or stereoisomer thereof.

to stereoisomers, of a compound according to the present disclosure which are the R or S enantiomer.

to tautomers of a compound according to the present disclosure which are the keto or enol form.

The neuropathic pain syndrome according to the present disclosure may be postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., postmastectomy syndrome, postthoracotomy syndrome, phantom pain), and complex regional pain syndrome (reflex sympathetic dystrophy and causalgia).

In some embodiments, the neuropathic pain is a central pain syndrome caused by spinal cord injury.

In some embodiments, the neuropathic pain is a central pain syndrome caused by a spinal cord contusion.

The present disclosure pertains also to pharmaceutical compositions for the use in the treatment of neuropathic pain and neuropathic pain syndromes comprising a malononitrilamide in free form or in the form of pharmaceutically acceptable salt or physiologically functional derivative, together with pharmaceutically acceptable diluents or carriers.

The present disclosure pertains further to pharmaceutical compositions for the use in the treatment of neuropathic pain and neuropathic pain syndromes comprising a compound of formula II in free form or in the form of pharmaceutically acceptable salt or physiologically functional derivative, together with pharmaceutically acceptable diluents or carriers.

Furthermore, the present disclosure pertains further to pharmaceutical compositions for the use in the treatment of neuropathic pain and neuropathic pain syndromes comprising a compound of one of the compounds with the formula II to V in free form or in the form of pharmaceutically acceptable salt or physiologically functional derivative, together with pharmaceutically acceptable diluents or carriers.

The present disclosure pertains further to pharmaceutical compositions for preventing and/or treating neuropathic pain and neuropathic pain syndromes, which comprises a therapeutically effective amount of a malononitrilamide or a physiologically functional derivative thereof in admixture with a pharmaceutical acceptable carrier or excipient.

The present disclosure pertains further to pharmaceutical compositions for preventing and/or treating neuropathic pain and neuropathic pain syndromes, which comprises a therapeutically effective amount of a compound with the formula II or a physiologically functional derivative thereof in admixture with a pharmaceutical acceptable carrier or excipient.

The present disclosure pertains further to pharmaceutical compositions for preventing and/or treating neuropathic pain and neuropathic pain syndromes, which comprises a therapeutically effective amount of a compound of one of the compounds with the formula II to V or a physiologically functional derivative thereof in admixture will a pharmaceutical acceptable carrier or excipient.

The treated neuropathic pain syndrome may be postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., postmastectomy syndrome, postthoracotomy syndrome, phantom pain), and complex regional pain syndrome (reflex sympathetic dystrophy and causalgia).

In some embodiments the neuropathic pain is a central pain syndrome caused by spinal cord injury.

In some embodiments the neuropathic pain is a central pain syndrome caused by spinal cord contusion.

We claim:

1. A method for treating chronic neuropathic pain, comprising: administering to a subject in need thereof a compound according to the formula

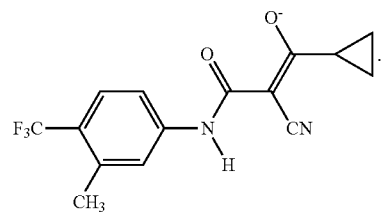 [SMILES: Cc1cc(NC(=O)/C(C#N)=C(\[O-])C2CC2)ccc1C(F)(F)F]

2. The method of claim 1, wherein the compound is administered at a daily dosage of between 1 mg-10 g/body beginning after a damage of the nervous system.

3. The method of claim 1, wherein the compound is administered a daily dosage of between 5 mg-5 g/body after a damage of the nervous system.

4. The method of claim 1, wherein the compound is administered a daily dosage of between 10 mg-2 g/body beginning after a damage of the nervous system.

5. The method of claim 1, wherein the compound is administered to the subject orally.

* * * * *